United States Patent [19]

Hagemeyer et al.

[11] Patent Number: 5,866,737
[45] Date of Patent: Feb. 2, 1999

[54] OXIDATION AND OXYDEHYDROGENATION OF HYDROCARBONS IN THE FLUIDIZED BED

[75] Inventors: Alfred Hagemeyer, Ludwigshafen; Jürgen Schweinzer, Frankenthal; Otto Watzenberger, Ludwigshafen, all of Germany

[73] Assignee: BASF Aktiengesellschaft, Ludwigshafen, Germany

[21] Appl. No.: 779,840

[22] Filed: Jan. 7, 1997

[30] Foreign Application Priority Data

Jan. 19, 1996 [DE] Germany .................. 196 01 750.5

[51] Int. Cl.⁶ .............. C07C 5/42; C07C 5/09; C07C 5/327; C07C 5/333
[52] U.S. Cl. .......... 585/443; 585/380; 585/621; 585/658; 585/943; 585/617; 585/444; 585/448; 585/634; 585/668; 585/676; 585/678; 585/630; 585/636; 585/601; 585/667; 585/663
[58] Field of Search .............. 585/440, 443, 585/444, 445, 380, 607, 621, 624, 625, 626, 629, 630, 631, 658, 661, 662, 663, 943

[56] References Cited

U.S. PATENT DOCUMENTS

| | | | |
|---|---|---|---|
| 3,842,132 | 10/1974 | Lo et al. | 585/379 |
| 4,067,924 | 1/1978 | Manning | 585/445 |
| 4,737,595 | 4/1988 | Jones et al. | 585/654 |

FOREIGN PATENT DOCUMENTS

| | | |
|---|---|---|
| 336 622 | 10/1989 | European Pat. Off. . |
| 403 462 | 12/1990 | European Pat. Off. . |
| 482 276 | 4/1992 | European Pat. Off. . |
| 1161257 | 9/1956 | Germany . |
| 44 23 347 | 7/1994 | Germany . |
| 44 22 770 | 1/1996 | Germany . |
| WO 81/01489 | 5/1981 | WIPO . |
| WO 96/01796 | 1/1996 | WIPO . |

OTHER PUBLICATIONS

Gas–Solid Systems, Sec. 20, Porter et al., Chem. Engineers' Handbook, McGraw–Hill, Chem. Engg. Series 6, Aufl. 1973, pp. 1–75.

*Primary Examiner*—Glenn Caldarola
*Assistant Examiner*—Thuan D. Dang
*Attorney, Agent, or Firm*—Keil & Weinkauf

[57] ABSTRACT

A process for the oxidation and oxidative dehydrogenation of hydrocarbons, in particular ethylbenzene, to form corresponding oxidized or olefinically unsaturated compounds, in particular styrene, over an oxygen-conferring, oxygen-regenerable catalyst involving a working period, a time-displaced regenerating period and at least one intermediate rinsing period comprises effecting a partial regeneration during the working period by time-displaced addition of a substoichiometric amount of oxygen.

11 Claims, 1 Drawing Sheet

OXIDATION AND OXYDEHYDROGENATION OF HYDROCARBONS IN THE FLUIDIZED BED

BACKGROUND OF THE INVENTION

1. Field of the Invention

The present invention relates to a process for preparing olefinically unsaturated compounds such as, in particular, styrene by oxidation or oxidative dehydrogenation in the gas phase by means of redox catalysts in the fluidized bed.

Styrene monomer (SM) is an important monomer for engineering plastics and is used in large amounts. It is prepared virtually exclusively by (nonoxidative) dehydrogenation of ethylbenzene (EB) at about 600° C. The dehydrogenation is an equilibrium reaction which is carried out on an industrial scale so that a conversion of about 60–70% is achieved and unconverted EB is thereafter separated off and recycled. The reaction is endothermic.

Complete conversion is only possible with processes which permit removal of the hydrogen from the reaction mixture. Oxidative dehydrogenation, which is exothermic, has therefore been suggested as a way of overcoming the equilibrium.

2. Description of Related Art

In conventional (direct) oxidative dehydrogenation, oxygen is fed together with the reaction mixture and passed over a single catalyst, generally of the fixed type. Water forms and is removed from the reaction equilibrium, so that virtually quantitative conversion is achieved at a relatively low temperature. Since oxygen is usually used in excess, the deposition of byproducts (coking) on the catalyst is not overly critical and it is possible in this way to maintain a steady state process over long periods and achieve a high space-time yield. A disadvantage of oxidative dehydrogenation is the occurrence of hitherto unavoidable side reactions which lead to total oxidation and hence loss of product of value.

To avoid this disadvantage, EP-A-0 336 622 proposes employing a plurality of catalyst systems by providing initially two or more dehydrogenation zones and feeding the oxygen-containing gas in at a plurality of points and then passing the product stream over an oxidation catalyst. For the dehydrogenation of ethylbenzene it is suggested that a conventional iron oxide catalyst be coupled with a downstream noble metal oxidation catalyst.

Another way of avoiding the direct contact of the reactants with free oxygen is based on the separation of the elementary steps of the reaction in space or time by means of a redox catalyst acting as an oxygen store and transfer agent. This process is known as an unsteady state or indirect process and has been proposed for various chemical reactions. Examples are the unsteady state oxidation and ammonoxidation of propene, the oxidative dehydrogenation of alkanes and alcohols, the oxidative dehydrogenation of mono- to diolefins, the oxidative coupling of methane to form higher hydrocarbons, the dehydrodimerization of toluene to stilbene, the dehydrocyclization and dehydroaromatization of paraffin hydrocarbons, the oxidation of butadiene and the oxidation of butane. Bi- and V-containing redox catalysts are mentioned as possible catalysts.

The redox catalyst catalyzes the hydrocarbon oxidation reactions by giving off lattice oxygen to form water and is reduced at the same time. The reduced catalyst is subsequently reoxidized by molecular oxygen. During the regeneration step any coke deposits on the catalyst are removed as well, so that the original activity is generally completely restored. The cycle is constantly repeated.

The unsteady state procedure is implemented in industrial practice in processes for waste gas cleanup, SCR removal of nitrogen oxides and in sulfuric acid production. Spatial separation on an industrial scale is also practiced in the case of cat crackers, where the cracking reaction and the subsequent regeneration of the catalyst to burn off coke deposits are separated in space via circulating fluidized bed reactors. Catalytic reforming (isomerization of hydrocarbons in the refinery art) is carried out using a migrating bed. It has also been proposed to employ spatial separation in a riser-regenerator fluidized bed for the oxidation of butane to maleic anhydride, and an unsteady state process is also used in industry for the dehydrogenation of propane (Catofin process). Four separate, adiabatic fixed bed reactors are used, which successively pass through the operating modes of dehydrogenation—rinsing—regeneration—rinsing.

According to EP-A-039 737 and EP-A-403 462, the principle of unsteady state reaction management can be used for the oxidative dehydrogenation of ethylbenzene to styrene, and numerous redox-active elements are named as useful catalyst components. Preference is given to V/MgO. The unsteady state dehydrogenation is also described in U.S. Pat. No. 4,067,924 with Mg-chromite catalysts and in U.S. Pat. No. 3,842,132 with Bi—Cr vanadates.

According to a proposal unpublished at the priority date of the present invention, Bi- and V-containing catalyst systems can be used for the oxidative dehydrogenation of ethylbenzene to styrene. Preference is given to the $K/Cs/La/Bi/TiO_2$ catalyst.

In unsteady state operation, conversion and selectivity are not constant over the operating cycle. At the start the catalyst is, say, in the oxidized state and is highly active. The reaction rate is correspondingly high, which also entails a certain increase in the byproduct level (gasification to carbon oxides, for example) associated with an arithmetically lower selectivity. As the degree of reduction of the catalyst increases, byproduct formation decreases and selectivity improves continuously to an end value specific to the particular catalyst employed. On the other hand, the catalyst becomes more and more deactivated at the rate of consumption of its lattice oxygen, so that the conversion decreases and the catalyst finally has to be regenerated. The net result is that the styrene yield, being the product of selectivity and conversion, generally passes through a flat maximum.

In industrial practice, the catalyst will not be used until it is completely deactivated; instead, regeneration will be initiated while conversion is still economically acceptable. Because the catalyst was only partially reduced, the regenerating time can be shorter, too.

Partial prereduction with H2 or CO has been proposed as a remedy against initial gasification (EP-A-482 276, JA-A-133 602, JA-A-127 819).

An advantage of unsteady state oxidation and oxydehydrogenation over direct oxidation is in any event the selectivity gain through a reduction in total combustion, since reactants and oxygen are no longer present in the reaction mixture at one and the same time. There are also advantages in the workup ("integrated separation process"). A disadvantage, on the other hand, is the relatively low space-time yield, since no product of value is produced during the regenerating period and in the rinsing periods. In the unsteady state oxydehydrogenation of ethylbenzene to styrene the cycle would typically have to consist of 15 minutes each of dehydrogenation and regeneration and two rinsing periods of 5 minutes each, resulting in a productive period of 15 minutes and waiting times of 25 minutes in total. This would require large catalyst masses and correspondingly large reactors.

SUMMARY OF THE INVENTION

It is an object of the present invention to increase the space-time yield in the oxidative dehydrogenation of hydrocarbons to form corresponding, olefinically unsaturated compounds over a regenerable, oxygen-transferring catalyst.

We have found that this object and others are achieved by a process for the oxidative dehydrogenation of hydrocarbons involving an operating period (ie. a period during which the product of value is formed), a time-displaced regenerating period and at least one rinsing period, which comprises effecting a partial regeneration during the working period by time-displaced addition of a substoichiometric amount of oxygen.

The invention exploits the surprising discovery that the susceptibility of the oxidative dehydrogenation reaction over a regenerable, oxygen-transferring catalyst to side reactions in the simultaneous presence of oxygen is decreased if the catalyst is already partially reduced, ie. no longer has its full transfer capacity.

According to the invention, this is achieved when the catalyst is disposed in a fluidized bed, which is presumably because, in this case, the catalyst particles are constantly completely backmixed, ie. are always in the same oxidation state, so that the advantages of prior art arrangements and procedures—high selectivity of the unsteady state process and high space-time yield of the steady state process—are combined and their disadvantages are substantially avoided.

Fluidized bed reactors and their use are well known. The principles of the fluidized bed process are described for example in Fluidization Engineering by Daizo Kunii and Octave Levenspiel, 2nd edition, 1991. An overview of the theory of gas-solids fluidization, various operating states, design aspects and a multiplicity of practical examples as found in Perry's Chemical Engineers' Handbook (McGraw-Hill Chem. Engg. Series), 6th edition, 1973, pages 20–58 to 20–75. A comprehensive survey of gas-solids fluidization with very extensive references is also given by Cheremisinoff, Nicholas, Hydrodynamics of Gas-Solids Fluidization, Houston 1984.

The invention is illustrated for the oxidative dehydrogenation of ethylbenzene to styrene, but can be used with advantage for other reactions as well.

It is suitable for example for the industrial practice of oxidative dehydrogenation reactions of aliphatics to olefins; mono- to diolefins; of cycloalkanes to aromatics; of alcohols to aldehydes/ketones; of aliphatics and olefins to oxygenates; also for the dehydrocyclization and dehydroaromatization of aliphatics and naphthenes to form aromatics; for the oxidative coupling of methane to form $C_2$ species or of toluene to form stilbene; for the ammonoxidation of aliphatics and olefins; for the oxidation and ammonoxidation of sidechain aromatics to sidechain oxygenates or nitriles.

The essential characteristic of the invention is thus the combination of a catalyst in a fluidized bed; use of a regenerable redox catalyst; and time-delayed substoichiometric addition of oxygen during the oxidation/dehydrogenation period (working period). The reaction regime of this invention is neither a conventional steady state procedure (continuous simultaneous addition of starting material and oxidant), nor a purely unsteady state procedure (addition of starting material in the absence of gaseous oxygen); on the contrary, it combines the advantages of these two known techniques and avoids their disadvantages.

Delayed substoichiometric addition of oxygen maintains the redox catalyst at all times in the partially reduced and hence highly selective state. This provides distinctly higher selectivity than steady state dehydrogenation and also a significantly longer cycle time compared with unsteady state dehydrogenation. The process is tied to the use of a fluidized bed, since this is the only way of providing an approximately uniform, spatially homogeneous state for all catalyst particles.

It is advantageous to keep the volume stream of the fluidizing gases constant by admixing the inert gas with oxygen or air in the appropriate amount. In effect, the substoichiometric addition of oxygen is thus brought about by the partial replacement of the inert gas—usually nitrogen—by air, for example. With the addition of oxygen it is thus possible, in order to maintain a constant total gas flow, to reduce the carrier gas stream, which advantageously reduces the inert gas consumption.

Since the phenomenon of coking, ie. the formation of deposits on the catalyst, cannot be completely avoided, the working period is discontinued at a time to be determined from case to case and replaced by complete reoxidation. After the reoxidized state has been obtained, the catalyst is first rinsed, operated for a suitable period with oxygen excluded, and oxygen is finally readmitted in a substoichiometric amount.

A secondary phenomenon under substoichiometric oxygen addition is the heat response of the arrangement of this invention. As the catalyst's degree of reduction increases and it consequently becomes more and more selective, the endothermic dehydrogenation of ethylbenzene has hitherto usually been accompanied by a decrease in the temperature; the deactivation speeds up even further. Since, however, the reoxidation of the partially reduced metal oxide is strongly exothermic, the recharging of the oxygen store according to the invention will result in a temperature increase; this can increase the mobility of the chemically stored oxygen and hence catalyst efficiency without leading to losses in selectivity. The result is an in situ temperature ramp, and the deactivation slows down further.

Compared with a fixed bed, a fluidized bed also has the advantage of better mass transfer, since the catalyst particles are comparatively small, and further the advantage of a lower temperature increase during regeneration (homogeneous temperature distribution, no hot spots owing to good backmixing).

Further advantages of the fluidized bed are the very good heat transfer between the fluidized bed and the existing heat exchanger surfaces for indirect heat removal, for example by steam generation. The fluidity of the solids also makes it easier, compared with the fixed bed, to introduce or remove the catalyst. In addition, no explosion limits have to be observed within a fluidized bed, since the high heat capacity of the solid suppresses the propagation of an explosion front.

The time delay of the oxygen injection relative to the hydrocarbon feed can be up to, for example, 3600 seconds in a specific case, preferably up to 1800, particularly preferably from 30 to 900, seconds, and has to be determined experimentally from case to case. Preferably the addition of oxygen is commenced when the styrene yield has just passed through its maximum and is beginning to decrease.

From 1 to 99, preferably from 5 to 95, particularly preferably from 10 to 90, mol % of the oxygen required for a stoichiometric reaction with the oxidizable hydrocarbon also present are held available in the reaction space. Preference is given to using air as reoxidant (dilution effect), and it is also necessary to take account of the total gas rate required for maintaining the fluidizing point. Care must also be taken to ensure that the explosion limits for the hydrocarbon in question are not exceeded when oxygen-containing gas is added below the fluidizing plate. This restriction does not apply when the oxygen is added separately, ie. into the reaction space in the region of high solids concentration.

The oxygen concentration can be varied with the reaction time in the form of a concentration ramp, so that the increasing deactivation of the oxygen store is offset by increasing oxygen content (the higher the degree of reduction, the higher the air dosage), up to almost stoichiometric oxygen concentration. The lower the ratio of hydrocarbon to oxygen, the lower the coking and hence the longer the onstream time.

For the process of this invention to be used no significant oxidation of the hydrocarbon may take place in the homogeneous gas phase and the reoxidation rate of the reduced catalyst has to be sufficiently high, and the oxygen has to be incorporated into the lattice sufficiently rapidly (no unselective chemisorbed oxygen on the catalyst surface).

The catalyst should have a high attrition resistance, and retention or recycling of the catalyst fines entrained in the fluidizing gas stream is necessary.

Suitable catalysts are already available. They can be unsupported, combined with a binder or applied to a support selected from the group consisting of the clays, PILC, zeolites, aluminum phosphates, silicon carbide, silicon nitride, boron nitride and also the metal oxides selected from the group consisting of Al, Ba, Ca, Mg, Th, Ti, Si, Zn, Cr or Zr. The active component comprises at least one oxide selected from the group of the oxides of the elements Ag, As, Bi, Ce, Co, Cr, Cu, Fe, In, Mn, Mo, Nb, Ni, Sb, Sn, Pb, U, V and W with a plurality of oxidation states. Preference is given to Bi- and V-containing redox catalysts. It is similarly possible to use mixtures and reaction products of the elements mentioned. The catalysts may further include promoters, especially alkali metals, alkaline earth metals and/or rare earths.

Particular preference for the dehydrogenation of ethylbenzene is given to a $TiO_2$-supported catalyst including essentially bismuth, potassium and lanthanum.

Redox catalysts are prepared by known methods, for example by dry mixing, slurrying, impregnating, precipitating, coprecipitating, spray drying and subsequent calcination, ie. heating to a temperature of from 300° to 1000° C., in one or more stages. The raw materials required can be present for example as oxides, hydroxides, carbonates, acetates, nitrates or generally salts of the respective elements with inorganic or organic anions. Transition metal complexes can also be used. The calcination is carried out at temperatures at which the respective raw materials form the catalyst. The active component of the catalyst can be applied to a support or be blended with a binder. This also includes surface finishes such as, for example, porous silicate layers to improve the attrition resistance of the fluidizable product.

When rare earth metals are to be used for augmenting the performance, specifically lanthanum should not be used in the form of the oxide, $La_2O_3$, since the effect is then only minimal. Instead, the choice should be for lanthanum oxide carbonate, $La(OH)_3$, $La_2(CO_3)_3$ or organic lanthanum compounds, such as lanthanum acetate, lanthanum formate or lanthanum oxalate, which lead to a finely divided and surface-rich active lanthanum phase on calcination. A preferred calcining temperature for decomposing $La(Ac)_3$ to the active lanthanum phase is for example from 550° to 700° C.

BRIEF DESCRIPTION OF THE DRAWING

An example of a suitable fluidized bed reaction for carrying out the process of this invention is the reactor (1) depicted in FIG. 1, which has a cylindrical shape widened at the top and advantageously has a gas distributor plate (2) above which the catalyst bed (3a) is fluidized.

The reaction space (3) may be provided with a heat exchanger, for example in the form of tube coils or a tube bundle (4), which is used for establishing the right temperature for all operating states. The disposition of the heat exchanger can be vertical, horizontal, spiral or a combination thereof. Suitable heat transfer media are water, steam, heat transfer oils and salt melts.

Figure 1:
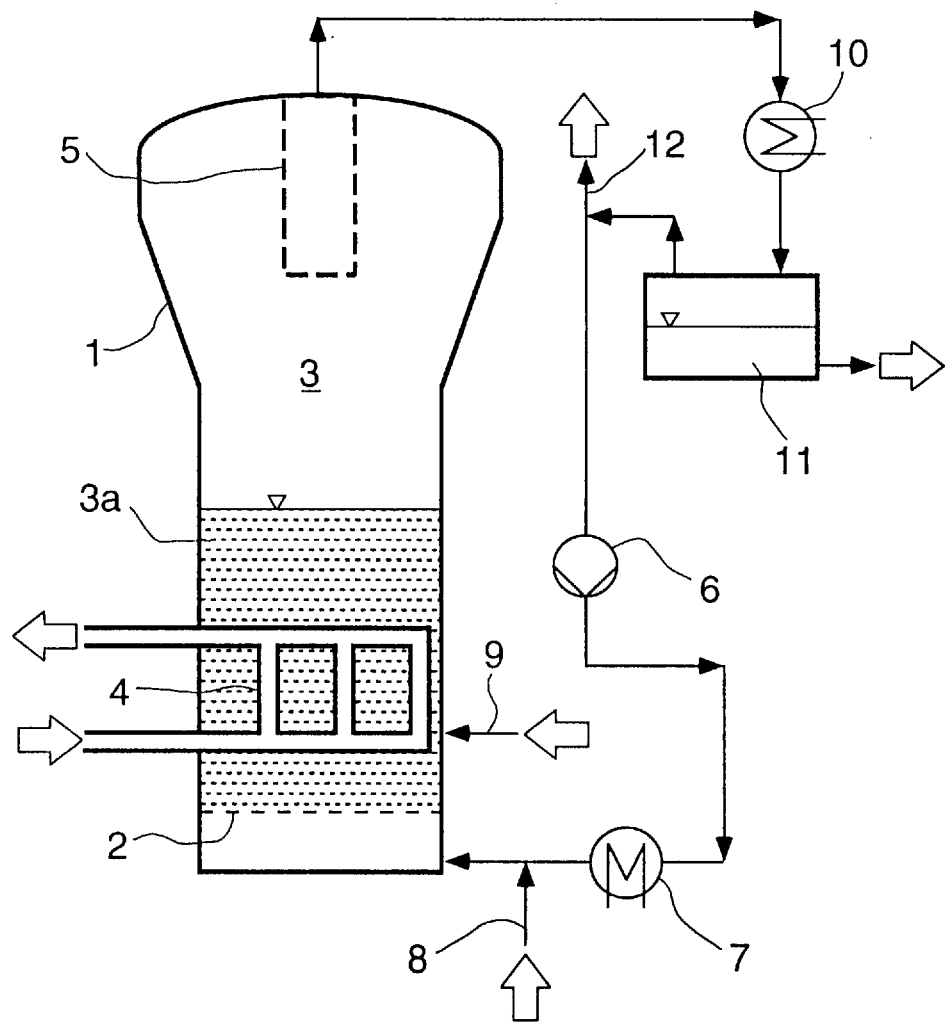

The reactor can be fitted with a solids retainer (5), for example in the form of filter candles or cyclones. However, the solids can also be separated off outside the reactor, with or without recycling of the collected solids into the reaction space.

The product leaving the reactor in gas form is separated from the carrier gas stream via a suitable separating system (10 and 11), for example in the form of a total condensation. The carrier gas can be recycled back into the reactor via a compressor (6) and heat exchanger (7) (recycled gas operation) or if desired be removed from the system via a gas purge (12). The raw starting material can be introduced either via the feed point (8) underneath the gas distributor, if necessary via a prevaporizer, or else (9) directly into the reaction space in liquid, vapor or partly condensed form.

The reoxidant can be introduced into the reactor in the same way as the starting material, ie. alternatively via the feed point (8) below the gas distributor plate (2) or above, at feed point (9); it is possible, of course, to split the feed between (8) and (9). It is advantageous to mix the reoxidant into the carrier gas.

The superficial gas velocity is for example within the range from 0.02 to 1.5 m/s. Preference is given to a gas velocity within the range from 0.05 to 0.45 m/s. Stationary bed height, expressed by the ratio H/D between height H and reactor diameter D, can be within the range from 0.1 to 10. Preference is given to a height which corresponds to an H/D ratio of from 0.5 to 5.

Liquids are preferably added directly to the reaction space with the aid of single-material or two-material nozzles.

The pressure drop in the gas distributor, $P_B$, is advantageously adapted to the pressure drop in the fluidized bed, $P_W$. The ratio $P_B/P_W$ is preferably within the range from 0.05 to 0.5, preferably from 0.1 to 0.3.

The oxidative dehydrogenation of ethylbenzene is carried out within the temperature range from 200° to 800° C., preferably from 350° to 600° C., within the pressure range from 100 mbar to 10 bar, preferably from 500 mbar to 2 bar, using a linear hourly space velocity (for ethylbenzene) within the range from 0.01 to 20 $h^{-1}$, preferably from 0.1 to 5 $h^{-1}$. Depending on the raw material, it can be added to the fluidizing bed alone or together with an appropriate diluent; in the simplest case the diluent is the carrier gas itself, for example $CO_2$, $N_2$, a noble gas or steam.

DESCRIPTION OF THE PREFERRED EMBODIMENT

The regeneration of the partially deactivated catalysts is carried out at temperatures within the range from 100° to 800° C., preferably from 250° to 600° C., using a free oxidant, preferably using $N_2O$ or an oxygen-containing gas including pure oxygen. Here too diluents can be present in the reactor feed stream. Also suitable are for example air or lean air. The regeneration can be carried out at reduced pressure, atmospheric pressure or superatmospheric pressure. Preference here too is given to pressures within the range from 500 mbar to 10 bar.

EXAMPLES

Preparation of the catalyst

The directions of DE-A-44 23 975 are followed as regards the use of a supported catalyst of the type $K_2O/La_2O_3/Bi_2O_3/TiO_2$, which is obtained as follows:

Potassium carbonate, lanthanum acetate, basic bismuth carbonate ($[BiO]_2CO_3$), and a commercially available $TiO_2$ support (DT-51; Rhone-Poulenc) are dry mixed and densified in a kneader for 2.5 h initially dry and then in the presence of water and a pore-former. The kneaded material is shaped in an extruder to 3 mm extrudates. They are dried at 120° C. for 16 h and calcined at 600° C. for 5 h, affording light yellow strands having a composition of 12.5% by weight of $K_2O$, 10% by weight of $La_2O_3$, 25% by weight of $Bi_2O_3$ and 52.5% by weight of $TiO_2$.

The BET surface area of the extrudates is 20.6 $m^2/g$, the cutting hardness is 11N per extrudate.

The extrudates are ground to grit size and a particle size fraction of from 0.064 mm to 0.4 mm is sieved out.

Reactor runs:

The catalytic oxidative dehydrogenation of EB to SM is carried out in a lab fluidized bed reactor.

Experimental setup

The experimental setup is illustrated in FIG. 2. The fluidized bed reactor has an internal diameter of 60 mm and a height of 700 mm in the cylindrical part. The reactor has a conical enlargement at the top (freeboard) to reduce the escape of solids and to accommodate ceramic filter candles. The cylindrical part of the reactor is made of quartz glass and is electrically heated by external heating coils. A metal frit serves as gas distributor.

The fluidizing gas ($N_2$, air or mixture) is rotametered into the reactor at a point below the gas distributor via an electrically operated, temperature-controlled gas heater. Ethylbenzene is metered via a capillary into the gas stream between gas heater outlet and fluidized-bed inlet using an HPLC pump. The reaction products leaving the reactor in gaseous form are condensed using two intensive condensers connected in series. At the lower end of the second condenser is a sampling point P and a means O for measuring the oxygen content. Two dry ice cold traps follow to remove condensable residual gases.

The reactor is filled via a side port in the region of the freeboard. Catalyst can be withdrawn via a radially disposed port directly above the gas distributor.

The reactor contains 3 thermocouples offset at different heights for detecting the reaction temperature. The uppermost thermocouple is also connected into the control circuit for the mantle heating. Filter cleaning by reverse flow is time-controlled.

Experimental procedure and conditions

The reactor is filled with catalyst (1625 g or 1542 ml) and heated up with preheated nitrogen and also by mantle heating to the starting temperature of from 490° C. to 550° C. for the reoxidation (regeneration). The gas rate setting is 430 standard 1/h, corresponding to a superficial gas velocity of 12.6 cm/s. On attainment of steady state conditions, atmospheric oxygen is mixed into the fluidizing gas. The temperature in the reactor rises by 30–40K within about 20 minutes, depending on the starting temperature, the degree of reduction of the preceding run and the amount of oxygen supplied. The oxygen supply is maintained until the temperature maximum has been exceeded and the temperature has again become steady state. This indicates the end of the oxidation process.

The oxidation period is followed by a short period of inertization with $N_2$, and if necessary the reactor can be heated up to the new starting temperature for the reaction. On attainment of the steady state the metered addition of ethylbenzene is commenced (start of the dehydrogenation period). The feed rate is 7.71 ml of EB/min.

2 minutes from the start of the addition of ethylbenzene an additional 63 standard 1/h of air is mixed in and the corresponding nitrogen rate is reduced accordingly, so that the gas velocity and hence the residence time remains constant.

The air supply remains open for 11 minutes. Subsequently, the runs are operated for a further 2 minutes only with $N_2$ as fluidizing gas. In total, during these runs, ethylbenzene is metered in for 15 minutes and the sampling is continued accordingly.

The cycle is completed by renewed reoxidation as described above.

The comparative run (purely unsteady state operation) differs essentially in that during the entire period of addition of ethylbenzene no air is added and the addition time for ethylbenzene is only 5 minutes in total.

The liquefied effluent is collected in ampoules and analyzed for ethylbenzene, styrene and byproducts (benzene and toluene). The respective levels are recorded in % by weight in the tables which follow.

Reoxidation of the deactivated reduced catalysts fully restored the catalytic activity. More than 40 cycles were measured, and no progressive activity loss as a function of the length of run was observed.

EXAMPLE 1

Invention

| Sampling | Conversion | Styrene yield |
|---|---|---|
| [minutes] | [%] | [%] |
| 3.5 | 98.85 | 78.46 |
| 4.5 | 98.71 | 79.49 |
| 5.5 | 98.71 | 80.98 |
| 6.5 | 98.47 | 82.02 |
| 7.5 | 98.33 | 82.97 |
| 8.5 | 98.20 | 83.52 |
| 9.5 | 98.06 | 83.67 |
| 10.5 | 97.92 | 83.88 |
| 11.5 | 97.78 | 84.14 |
| 12.5 | 97.69 | 84.04 |
| 13.5 | 97.66 | 84.04 |
| 14.5 | 97.67 | 83.74 |
| 15.5 | 97.70 | 83.74 |
| 16.5 | 97.77 | 83.67 |
| 17.5 | 97.74 | 83.64 |
| 20.5 | 97.88 | 82.33 |
| Comparative (purely unsteady state) | | |
| 3 | 98.22 | 81.42 |
| 3.5 | 98.02 | 81.76 |
| 4 | 97.88 | 82.46 |
| 4.5 | 97.81 | 83.40 |
| 5 | 97.78 | 84.23 |
| 5.5 | 97.75 | 84.79 |
| 6 | 97.76 | 85.35 |
| 6.5 | 97.74 | 85.66 |
| 7 | 97.73 | 86.52 |
| 7.5 | 97.73 | 87.70 |
| 8 | 97.74 | 88.66 |
| 8.5 | 97.79 | 89.29 |
| 9 | 97.82 | 91.49 |

Conclusion

Delayed substoichiometric addition of oxygen (catalyst in the partially reduced state) made it possible to prolong the dehydrogenation period by a factor of from 2 to 3 compared with the purely unsteady state procedure, and a maximum styrene yield of about 84% at almost 98% conversion was achieved. The selectivity (not optimized) is somewhat lower than under unsteady state operation.

We claim:

1. A process for oxidative dehydrogenation of hydrocarbons to form corresponding olefinically unsaturated compounds over a redox catalyst which comprises the steps of:

(1) filling a fluidized-bed reactor with the catalyst;

(2) feeding a fluidizing gas and hydrocarbons in the absence of free oxygen into the fluidized-bed reactor wherein the hydrocarbons come into contact with the catalyst;

(3) adding an oxidant containing substoichiometric mol % of oxygen with respect to hydrocarbons during the oxidative dehydrogenation period after steady state conditions have been attained;

(4) feeding the hydrocarbon in the absence of free oxygen to the fluidized-bed reactor where it comes into contact with the redox catalyst during the oxidative dehydrogenation period;

which results in the hydrocarbon being oxidatively dehydrogenated while the redox catalyst is regenerated.

2. The process as claimed in claim 1, wherein the volume flow of the fluidizing gas into the fluidized bed is kept constant regardless of the presence or absence of oxygen.

3. The process as claimed in claim 1, wherein the fluidized bed comprises at least one oxygen-conferring metal oxide redox catalyst selected from the oxides of Bi, V, Ce, Fe, In, Ag, Cu, Co, Mn, Pb, Sn, Mo, Sb, As, Nb, U, W or mixtures thereof, optionally provided with an inorganic binder or applied to a support selected from the group consisting of the clays, zeolites, SiC, $Si_3N_4$, AlPOs, PILCs or metal oxides selected from the group of the oxides of Ti, Zr, Zn, Th, Mg, Ca, Ba, Si, Al, Cr or mixtures thereof.

4. The process as claimed in claim 1, wherein an alkylaromatic compound or a paraffin hydrocarbon is oxidatively dehydrogenated to give the corresponding alkenylaromatic or olefin.

5. The process as claimed in claim 4, wherein ethylbenzene is dehydrogenated to styrene.

6. The process as claimed in claim 5, wherein the oxidative dehydrogenation of ethylbenzene is carried out within the temperature range from 200° to 800° C., at a pressure of from 100 mbar to 10 bar and using a liquid hourly space velocity (LHSV) of from 0.01 to 20 $h^{-1}$.

7. The process as claimed in claim 1, wherein $N_2O$ instead of oxygen is used as an oxidant.

8. The process as defined in claim 1 for the oxidative dehydrogenation of aliphatics to olefins;

of monoolefins to diolefins;

of cycloalkanes to aromatics; or of aliphatics and olefins to oxygenates.

9. The process as defined in claim 1 for dehydrocyclization and dehydroaromatization of aliphatics and naphthenes to aromatics.

10. The process as defined in claim 1 for oxidative coupling of methane to C2 species; or of toluene to stilbene.

11. The process as claimed in claim 1, wherein addition of the oxygen gas stream requires a time delay of up to 3600 s.

* * * * *